United States Patent [19]

Lee

[11] Patent Number: 5,088,927
[45] Date of Patent: Feb. 18, 1992

[54] RADIO OPAQUE PLASTICS AND PROCESS OF MAKING

[76] Inventor: Howard G. Lee, 721 32 Ave., Hudson, Wis. 54016

[21] Appl. No.: 539,807

[22] Filed: Jun. 18, 1990

[51] Int. Cl.$^5$ ............................................. A61C 5/02
[52] U.S. Cl. ................................ 433/224; 433/201.1; 623/11
[58] Field of Search ............ 433/220, 221, 224, 228.1, 433/173, 201.1; 623/11, 16

[56] References Cited

U.S. PATENT DOCUMENTS

| | | | |
|---|---|---|---|
| 3,715,331 | 2/1973 | Molnar | 260/41 |
| 3,786,808 | 1/1974 | Lerner | 128/839 |
| 3,801,344 | 4/1974 | Dietz | 433/228.1 |
| 3,808,170 | 4/1974 | Rogers | 260/42.53 |
| 3,959,212 | 5/1976 | Rockett et al. | 106/35 |
| 3,971,754 | 7/1976 | Jurecic | 260/42.15 |
| 3,973,972 | 8/1976 | Muller | 106/35 |
| 3,974,104 | 8/1976 | Foster et al. | 106/35 |
| 4,017,454 | 4/1977 | Müller | 260/42.52 |
| 4,032,504 | 6/1977 | Lee, Jr. et al. | 106/35 |
| 4,106,506 | 8/1978 | Koehn et al. | 604/164 |
| 4,220,582 | 9/1980 | Orlowski et al. | 433/228.1 |
| 4,297,266 | 10/1981 | Ibsen et al. | 106/35 |
| 4,311,528 | 1/1982 | Dietz et al. | 106/35 |
| 4,326,889 | 4/1982 | Sperner | 106/35 |
| 4,375,967 | 3/1983 | Schaefer | 433/199 |
| 4,516,970 | 5/1985 | Kaufman et al. | 604/270 |
| 4,629,451 | 12/1986 | Winters et al. | 604/175 |
| 4,758,156 | 7/1988 | Johnson | 433/81 |

FOREIGN PATENT DOCUMENTS 0231838  8/1987  European Pat. Off. ............ 433/173

Primary Examiner—John J. Wilson
Attorney, Agent, or Firm—Jacobson & Johnson

[57] ABSTRACT

A plastic article having heavy metal particles uniformly dispersed throughout the plastic article to produce a plastic article that is visible on an x-ray image of the plactic with one embodiment of the plastic article forming a solid tooth implant covered with a flowable gutta-percha filler material for insertion into the root canal of a tooth wherein a photoshadowgraph of a tooth containing the solid tooth implant and a solidified gutta-percha covering appears as a single image with the preferred mixture for the solid implant composition consists of about 50% by weight of a polymer plastic pellets and the balance about 50% by weigh of heavy metal particles selected from the group consisting of tungsten and tantalum particles.

15 Claims, 2 Drawing Sheets

RADIO OPAQUE PLASTICS AND PROCESS OF MAKING

FIELD OF THE INVENTION

This invention relates generally to radio opaque plastic compositions, methods of making the radio opaque plastic compositions, and articles made from the radio opaque plastic composition for use as an implant in a human. In one embodiment my radio opaque plastic composition together with a separate filler material can be used as a filling for a tooth. When a tooth is filled with my radio opaque plastic composition and a second filler material and then subjected to x-rays examination it surprisingly produces a photoshadowgraph image wherein the two separate filler materials appear as a single material with no visible interface shading.

BACKGROUND OF THE INVENTION

Polymer plastics because of there inherent characteristics are often preferred for use in medical applications such as tooth and bone implants. Unfortunately, one of the problems with plastics is that when the implanted plastic article is subjected to x-rays the resulting image of most plastics is not detectable on the x-ray picture. In order to solve this problem it is well known to mix metals or other materials into the plastics to produce a material that when x-rayed produces an x-ray picture that contrasts with the body. One of the difficulties with mixing polymer plastics with metals or other radio opaque compounds is that it weakens the plastic. In some cases this can be tolerated but in other cases substantial weaken of the plastic is not acceptable.

Another difficulty is to mix materials into the plastic to improve the radio opacity of the plastics without having the added materials effect the mixing process. For example, heating a composition of a plastic and a radio opaque additive to the melting temperature of the plastic so that one can mold the composition into a homogeneous product may result in oxidation of the added materials. Consequently, when mixing radio opaque materials into the polymer plastics one must prevent the molding process of the plastic and the radio opaque materials from interfering and destroying each other. The present invention solves the problem of mixing radio opaque materials into certain polymer plastics to produce a molded plastic product is radio opaque so that when the x-rayed the presence of the molded plastic product appears on an x-ray picture of the molded plastic product.

Another difficulty with use of plastic materials in place of metals is that even if materials have been added to the plastic to make the plastic radio opaque the radio opacity of the resulting material may not have the correct degree of radio opacity for the particular application. For example, in one application, which is described in U.S. Pat. No. 4,758,156, a cone of gutta-percha is placed outside of a tooth implant comprising an elongated shaft. The composite insert comprising the tooth implant and the gutta-percha is then inserted into a root canal of a tooth to form a filling for the tooth. If a metal is used as the tooth implant then the resulting x-ray image of the tooth with the filling comprising the combination of gutta-percha and the metal tool appears as a single image in an x-ray image of the tooth. Although two materials are present it is desired to have the x-ray image of the two materials appear as a single image in such applications. However, when one uses plastic in place of the metal in the tooth implant the resulting x-ray image appears as two distinct materials. One of the problems the present invention solves is to make two distinct materials appear as one image when subjected to x-rays. Not only is it necessary to make the two materials appear as one when x-rayed but it is also necessary to prevent the addition of radio opaque filler materials to the tooth implant from weakening the tooth implant. That is, if one mixes radio opaque materials into the filler material used to make the tooth implant the radio opaque material acts as a spacer and filler to the composition and may weaken the tool to the point where the tool is not sufficiently strong for use in the intended manner. When a tooth implant is used in the intended manner the user can insert both the tooth implant and a gutta-percha filler material into the bottom of the root canal without breaking the tool. Thus a person is faced with the simultaneous tasks of making a sufficiently strong tooth implant and also having two different filler materials that when x-rayed produce a single x-ray image without any interface areas between the two materials showing up as a void or cavity in the tooth.

The present invention involves a discovery that the combination of selected amounts of heavy metals with a thermoplastic polymer provides a radio opaque article. In addition it has been found that combination of selected amounts of heavy metals with a thermoplastic polymer filler material mixture also can be used to mold a body implant that is detectable by x-rays. It also has been discovered that the use of my composition in tooth implants for insertion into a root canal as a permanent implant is sufficiently strong to us to force gutta-percha filler material or gutta-percha like material and the tooth implant into a root canal. In addition, x-ray post examination of a tooth filled with a severed portion of a dental tool made from the composition of the present invention and a different filler material reveals a single image. That is, it has been discovered that when a tooth is x-rayed that contains an insert made from my invention that contains a combination of selected amounts of a heavy metals with a thermoplastic polymer that is surrounded by a layer of gutta-percha one obtains a single photoshadowgraph image. This single image occurs even tho two distinct material having distinct interfaces are located in the root canal. Consequently, even tho two different filler materials are located in a coaxially, separate relationship in a tooth, the x-ray image of the severed end of the tooth implant surrounded by a cone of gutta-percha appears as a single uniform image on an x-ray picture of a filled tooth. Ironically, the use of two different materials to create a false image of what is actually present in the tooth is preferred since it ensures that during a later x-ray examination of a filled tooth the practitioner will not be falsely deceived into believing that the tooth has a void or cavity.

Further background on the concept of applying filler material to an endodontically prepared root canal is described in U.S. Pat. No. 4,758,156. Briefly, the patent discloses a tooth implant having an elongated severable shaft coated with a cone of gutta-percha. To insert the tooth implant and the gutta-percha into a root canal the gutta-percha is heated to make it flowable. Then the elongated severable stiff but resilient end of the tooth implant with the flowable gutta-percha is used to push both the gutta-percha and the end of the tooth implant into the root canal. Once the gutta-percha and the elongated severable end of the tool compactly fill any voids in the root canal the user twists the handle of the tooth implant to break off the severable end of the tool thereby leaving both the severed end of the tooth implant and the gutta-percha as filler material in the root canal. Typically, the tooth implant is made of either a metal or a plastic so as to have sufficient strength and flexibility to permit a dentist to push both the elongated shaft of the tooth implant and the gutta-percha into the bottom of the root canal. Unfortunately, unless the shaft is metal a photoshadowgraph (commonly referred to as x-rays) or x-ray image of a tooth with two different filler materials appears on an x-ray picture as two distinct images with a void between the two filler materials. The appearances of two distinct x-ray images may lead false post x-ray examinations where the dentist is led to believe that the x-rayed tooth was not properly filled or that the tooth contains a cavity.

In order to eliminate false diagnose caused by the x-ray images produced by the two dissimilar materials one needs to eliminate the x-ray appearance of the two dissimilar materials that leads an observer to believe the tooth contains a cavity. The present invention solves the problem of making a plastic implant appear as the surrounding gutta-percha filler on an x-ray image of the plastic implant and the surrounding gutta-percha.

DESCRIPTION OF THE PRIOR ART

The concept of mixing metals or other radio opaque materials with polymer plastics or other filler materials to make normally radiotranslucent plastics detectable by means of X-rays is well known in the art. The following is a list of such prior art.

The U.S. Pat. No. 3,715,331 discloses an x-ray opaque material comprising a combination of a plastic and a metal to produce an x-ray opaque material comprised of methacrylate particles and compounds containing heavy metals such as tungsten with the heavy metals selected to provide the desired color characteristics to the filler material as well as to enhance the radioopacity of the material. The coloring materials including the heavy metal are hammered into the surface of the methacrylate particles.

The U.S. Pat. No. 3,801,344 discloses an x-ray opaque filling composition using a finely divided glass-ceramic material and barium aluminosilicate with a radio opaque oxide.

The U.S. Pat. No. 3,971,754 discloses an x-ray opaque enamel matching dental filling material having low toxicity that matches the color of the tooth with a ground glass filler containing compounds selected from the class consisting of oxides and carbonates of lanthanum, hafnium, strontium and tantalum.

The U.S. Pat. No. 3,808,170 discloses a translucent material that is opaque to x-rays. The material comprises an epoxy resin and a methacrylate acid compound crosslinked with a diester or triester of methacrylic acid as the matrix with a barium-containing glass filler.

The U.S. Pat. No. 3,973,972 discloses an x-ray opaque transparent tooth filling composition that contains metal oxides.

The U.S. Pat. No. 3,959,212 discloses a radio-opaque filler material that comprises a crystalline silicate containing barium in the crystalline composition.

The U.S. Pat. No. 3,974,104 shows a radio opaque filler material comprising a tin containing polymer.

The U.S. Pat. No. 4,017,454 discloses an x-ray opaque dental filling composition that uses glass ceramics in combination with any of a number of oxides.

The U.S. Pat. No. 4,375,967 discloses an x-ray opaque dental composition comprising a polymerizable matrix and a metal selected from the group consisting of calcium, strontium, barium, lanthanum, rare earth metals having an atomic number of 58–71, tantalum and hafnium.

The U.S. Pat. No. 4,326,889 discloses coating a dental prosthesis with gold.

The U.S. Pat. No. 4,311,528 discloses an x-ray opaque a root filler paste that uses calcium hydroxide, oleum pedum tauri and an x-ray contrast agent.

The U.S. Pat. No. 4,297,266 discloses an x-ray opaque dental composition where the filler is a mixture of hydrophobic silica particles with an X-ray opaque glass material.

The U.S. Pat. No. 4,220,582 discloses an x-ray opaque dental filling material that contains barium glass to enhance the X-ray opacity of the material.

The U.S. Pat. No. 4,032,504 discloses an X-ray opaque filling material for teeth that uses barium glass and an x-ray transparent particulate material that has substantially the same refractive index as the barium glass.

SUMMARY OF THE INVENTION

Briefly, the present invention comprises the discovery of radio opaque materials that can be easily molded with a thermoplastic such as polysulfone to produce a radio opaque plastic composition with the radio opaque material being a heavy metal selected from the group consisting of particles tungsten or tantalum. It has been found that the composition when molded into a tooth implant produces a solid dental filler material that when encapsulated with a gutta-percha filler material and inserted into a root canal to form a tooth filler and then subjected to x-rays produces a photoshadowgraph wherein the x-ray visual image of gutta-percha and the polymer plastic appear as an image of a single contiguous homogeneous material.

DESCRIPTION OF THE PREFERRED EMBODIMENT

Figure 1:
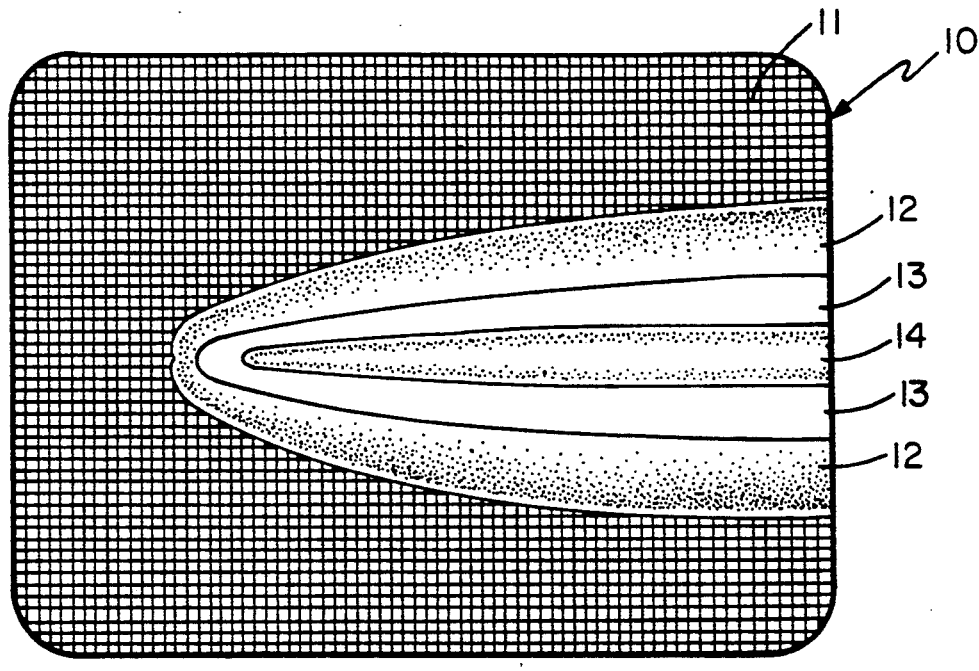
FIG. 1 shows a prior art photoshadowgraph or x-ray image of a portion of a tooth having a filling of a gutta-percha and a tooth implant made of a polymer plastic.

Referring to FIG. 1 reference numeral 10 generally identifies a prior art photoshadowgraph or an x-ray picture of the root end of a tooth 12 having a root canal filled with a portion of a severable solid tooth implant or carrier and a solidified gutta-percha. Reference numeral 11 indicates shading used to illustrate the black region that normally appears on x-ray pictures. The x-ray image illustrates that tooth 12 has an elongated root canal completely filled with the severed end 14 of a plastic tooth implant and an outer cone of gutta-percha 13. Even tho the gutta-percha and the severed end of the implant completely fill the void the resulting x-ray image has sufficient differences in shading that may lead one to falsely believe that the root canal is not completely filled when it is in fact completely filled by the severed end of the solid tooth implant and the solidified gutta-percha.

Figure 2:
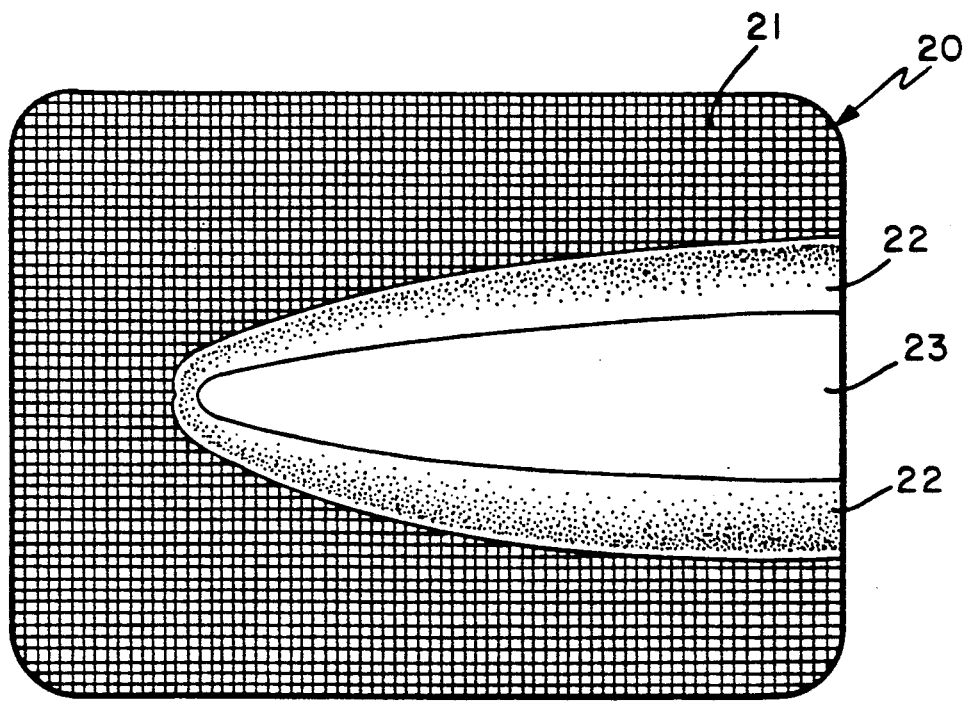
FIG. 2 shows a photoshadowgraph of the present invention showing an x-ray image of the root a tooth having a filling of a gutta-percha and a tooth implant formed from the composition of the present invention.

Referring to FIG. 2 reference numeral 20 identifies an x-ray image of the root end of a tooth 12 having a root canal filled with a portion of a severable solid tooth implant made of the present invention and a gutta-percha filler material. Reference numeral 21 indicates shading used to illustrate the black region that normally appears on x-ray pictures. The x-ray image illustrates tooth 22 has an elongated root canal that appears to have a region 23 completely filled with a single material. In fact the x-ray image in FIG. 2 is of two different filler materials, namely the severed end of a tooth implant made from the composition of the present invention and an outer cone of gutta-percha.

Figure 3:
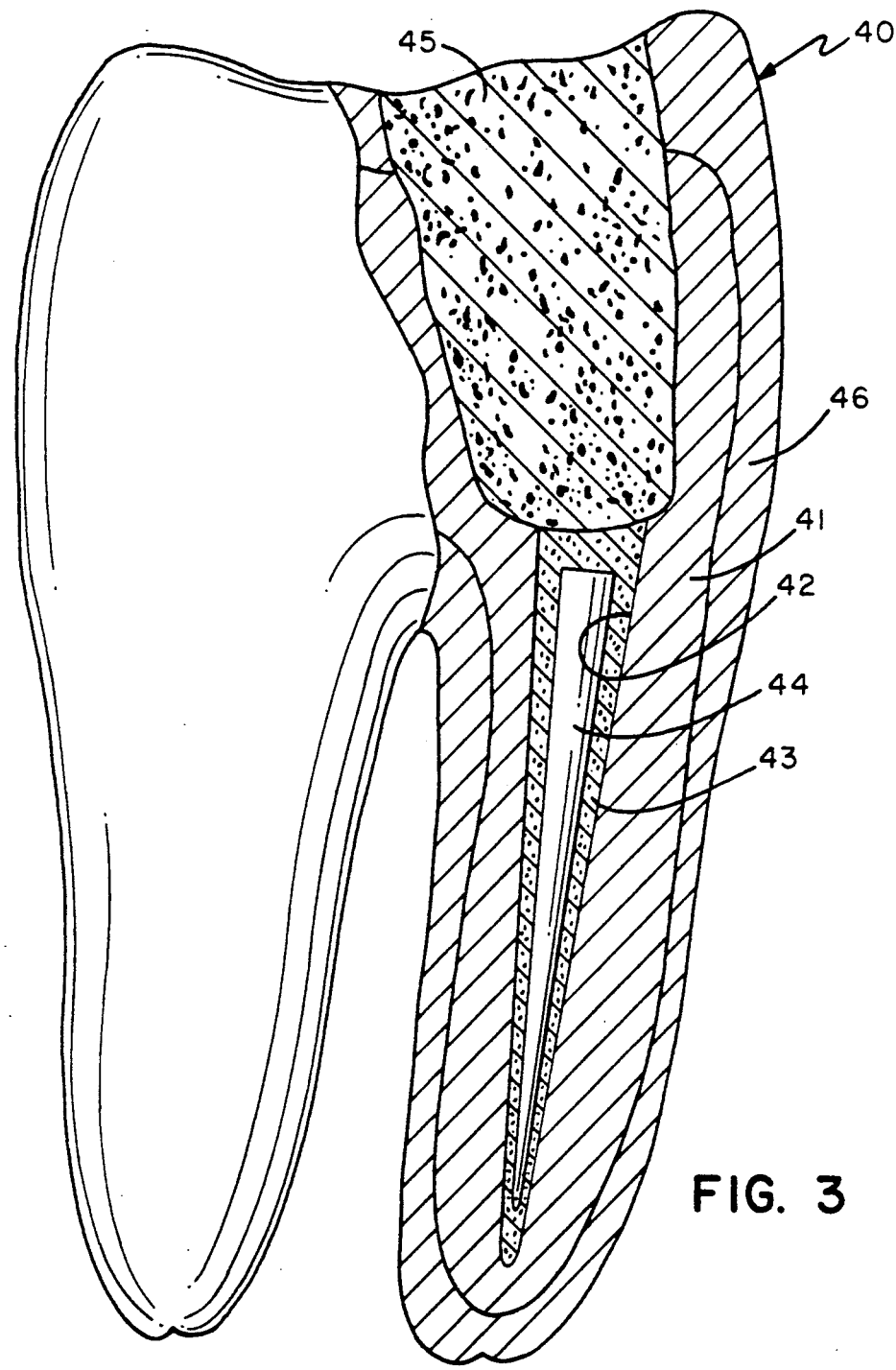
FIG. 3 shows a partial cross sectional view of a tooth having a filling of a tooth implant surrounded with an exterior encapsulating cone of filler material of gutta-percha.

Referring to FIG. 3 reference numeral 40 generally identifies a partial cross sectional view of a filled tooth. FIG. 3 shows tooth 40 has an outer layer of enamel. Located in tooth 40 is a solid metal filling material 45, a solid tooth implant 44 and a solidified gutta-percha filler material filling the cavity 42 in root 41 of tooth 40. For purposes of discussion only one of the roots of the tooth is shown but it should be understood that the other roots of the tooth can be filled in an identical manner. Located completely surrounding tooth implant 44 is an exterior cone of gutta-percha 35 that is used as one of the filler materials for filling a root canal. As described in the prior art Johnson U.S. Pat. No. 4,758,156 the combination of the rigid material of the tooth implant and the flowable gutta-percha allows one to use the combination of the solid tool and the flowable gutta-percha to completely fill the voids in a root canal. That is, in order to use the severable tooth implant as a carrier for insertion of the gutta-percha the tooth implant must be made of a material that is sufficiently rigid and flexible to permit one to insert and force both the flowable gutta-percha filler material and the solid filler material of the tooth implant into a root canal without breaking the tooth implant.

I have discovered that if I mix heavy metal particles of either tantalum or tungsten with approximate equal amounts by weight of a polysulfone thermoplastic that I can produce a tooth implant composition that when molded into a solid tooth implant such as tooth implant 44 produces a solid implant that has sufficient strength so as to perform its normal function of pushing both the severable end of the tooth implant and a flowable gutta-percha covering into a root canal. Furthermore, when subjected to x-rays an x-ray image of a tooth containing both the severed end of my tooth implant and the encapsulating gutta-percha appears as single image. FIG. 2 illustrates such an x-ray image where the x-ray image of a tooth containing both the severed end of the tooth implant and the gutta-percha appear as one continuous image.

EXAMPLE

In order to prepare my radio opaque composition I selected 100 grams of a medical grade polysulfone. The normally non radio opaque polysulfone material was in the form of pellets approximately ½ of a centimeter in diameter. Next I obtained 100 grams of tungsten metal particles that ranged from about 4 to 5 microns in diameter. Both the pellets and the particles were blended together to make a uniform mixture of tungsten particles and polysulfone particles that consisted of about 50% by weight of polysulfone particles and about 50% by weight of tungsten particles. In order to homogeneously disperse and encapsulate the tungsten particles into a molded product it was necessary to heat the polysulfone to the molding temperature of about 550 degrees Fahrenheit. Since the molding temperature was well below the melting temperature of the tungsten the tungsten particles retained there solid state. After heating the mixture the mixture was injected molded to produce an elongated shaft for insertion as a partial filler in a root canal.

In order to make a radio opaque body implant I used a high temperature medical grade polysulfone. In preparing mixtures of polymer plastic and metal particles I have discovered that in preparing the mixture in the atmosphere one must take care to observe the relationship between the injecting molding temperature of the plastic material and the size of the metal particles. For example, if the metal particles are two small in size and the injection molding temperature of the plastic is relatively high the particles may oxide and destroy the mixture. On the other hand if the size of the particles is to large the particles may retain heat to long and char the region around the particles as the plastic solidifies. In order to obtain; n the proper relationship between the size of the metal particles to mix with a particular polymer plastic one can select the particle size through trial and error. For example, I have found that mixing tungsten particles of a diameter of about 4 to 5 microns with a plastic that has an injection molding temperature of about 550 to 600 degrees in an air atmosphere can produce a solid radio opaque plastic of substantially the same strength as the original plastic.

If desired one can minimize the problems of destruction of the mixture by mixing and molding materials in an inert atmospheres. It should be pointed out that the heavy metal particles retain there characteristics when mixed with the polysulfone since the temperatures that the tungsten is subjected is sufficiently low so as not to melt the tungsten particles. Consequently, the resulting plastic is in effect a thermoplastic plastic with heavy metal uniformly dispersed throughout the plastic so that when an x-ray is taken of the molded article it appears as a metal article.

While tungsten was described as the preferred metal for mixing with polysulfone my invention will work equally well with tantalum particles.

After molding a tooth implant from a mixture of polysulfone pellets and tungsten particles an exterior cone of gutta-percha was placed on the outside of the tooth implant. After preparing the root canal the tooth implant 44 with the gutta-percha coating was heated to make the gutta-percha flowable. Next the tooth implant and the flowable gutta-percha were pushed into the root canal. After completing the filling of the tooth with a carrier of two different materials and an encapsulating layer of gutta-percha an x-ray of the tooth was taken. The x-ray image of the tooth appeared as in FIG. 2 as a single image even though different materials were present in the root canal.

During repeated testing and evaluation of the materials it was found that the best results were obtained if the weight of the tungsten in the tungsten polysulfone mixture were about equal with the tungsten ranged from a low of about 49.5% by weight to a high of about 51% by weight. That is, the physical characteristics of the solid tooth implant did not degrade to a point that would cause the tooth implant to perform unsatisfactorily. Also an x-ray image of the materials comprised of the severed end of the tooth implant made from the composition of example 1 and the encapsulating layer of gutta-percha clearly appeared as a single image on an x-ray image of filled tooth.

Although the preferred range of heavy metal particles is 49.5% to 51% by weight of the mixture of the thermoplastic and the heavy metal particles in certain applications one can use as little as 35% tungsten or tantalum to as much as 65% tungsten or tantalum. Generally, the more heavy metal particles that are added the better the solidified mixture shows up on an x-ray picture and the more tungsten or tantalum added the weaker the solidified mixture becomes.

While my invention has been described in relation to use with a filler material of gutta-percha it should be pointed out that other gutta-percha like filler materials having the same x-ray image as gutta-percha could also be used with a tooth implant formed from the composition of my invention. Likewise although polysulfone is described as the preferred filler material for use in the tooth implant other materials that are compatible for mixing with either tungsten or tantalum particles could be used to make the tooth implant.

Figure 4:
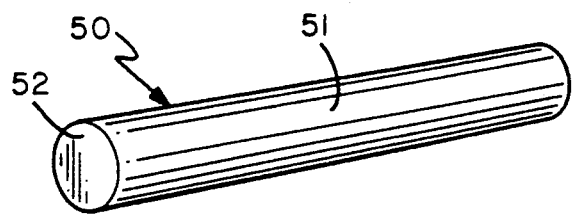
FIG. 4 shows an implant for use in the body that is radio opaque and has sufficient strength to perform the intended function in the body part.

In addition to use of my composition as a dental implant my composition can also be use for implants in other parts of the body. In such applications it is only necessary to have a plastic article that clearly shows up on an x-ray. FIG. 4 illustrates a plastic pin 50 that may be implanted in a bone. Plastic pin 50 has an outer cylindrical surface and an end surface 52. Pin 50 is molded from a composition consisting of about 50% by weight of polysulfone and about 50% by weight of tungsten. With the preferred range of tungsten and polysulfone there is virtually no loss in the inherent strength of pin 50. Consequently, pin 50 can be used as an implant and when subjected to x-rays produces and x-ray image like a metal article.

I claim:

1. An implant for a body part comprising:
   a solid rigid material for insertion into an artificially formed body cavity, said solid rigid material comprising a polymer plastic, said solid rigid material having an interior region and an exterior shape, said polymer plastic comprising polysulfone having tungsten particles uniformly distributed therethrough so that an x-ray image of a body part containing said solid rigid material shows the the interior region and the exterior shape of said solid rigid material in the body part to enable a person viewing an x-ray of the body part containing the implant to determine the shape and boundaries of said solid rigid material implanted in the artificially formed body cavity.

2. The implant of claim 1 wherein said polymer plastic is a thermoplastic.

3. The implanted of claim 1 wherein said tungsten in said solid rigid material ranges from a low of 35% by weight to a high of 65% by weight of the solid rigid material.

4. The implant of claim 1 wherein said polysulfone comprises about 49% to 50.5% by weight of the solid rigid material and said tungsten comprise about 49.5% to 51% by weight of said solid rigid material.

5. The implant of claim 1 wherein said said tungsten particles have a diameter of four to five microns.

6. An implant for filling an endodontically prepared root canal of a tooth, the canal extending from the tooth coronal areal to the root apex, said implant comprising:
   a flowable filler material;
   an elongated shaft for acting as a carrier for inserting said shaft and the flowable filler material into the root apex, said elongated shaft comprising a different material from the filler material with the improvement comprising the elongated shaft made from a polymer plastic having heavy metal particles dispersed therethrough with the heavy metal particles selected from the group consisting of tungsten and tantalum particles so that an x-ray image of said shaft and said filler material encasing said shaft appear as a single continuous image.

7. The implant of claim 6 wherein said polymer plastic comprises polysulfone and said heavy metal particles have a diameter of about 4 to 5 microns.

8. The process of making a radio opaque article for use as an implant comprising the steps of:
   selecting heavy metal particles having a diameter of about 2 to 5 microns from the group consisting of tungsten particles and tantalum particles;
   mixing said selected heavy metal particles with a pelletized thermoplastic until the heavy metal particles are blended uniformly through out the mixture;
   heating the mixture to the injection molding temperature of the polymer plastic to thereby make said plastic a liquid, said injection molding temperature sufficiently below the melting temperature of the solids so that the heavy metals particles remain as solid particles; and
   injecting molding the mixture into a mold to produce a radio opaque plastic article with solid metal particles dispersed therethrough so that an x-ray image of the radio opaque plastic appears as a single continuous image.

9. A tooth implant for filling a cavity in a tooth comprising at least two different components wherein a photo shadowgraph of a tooth with the filling of two different components appears as a single image comprising:
   a first tooth filling component, said first tooth filling component comprising a flowable material for insertion into the cavity in a tooth; and
   a second tooth filling component, said second tooth filling component comprising a molded carrier for coaxially holding said flowable material for insertion of both said first tooth filling component and said second tooth filling component into the cavity of a tooth, said molded carrier having a radio opaque material uniformly dispersed therethrough, said radio opaque material comprises about 50% by weigh of the mixture of said second tooth filling component wherein said radio opaque material is a heavy metal selected from the group of heavy metals consisting of tungsten and tantalum.

10. The tooth implant of claim 9 wherein the second filler material is polysulfone and said first tooth filling material is gutta-percha.

11. The tooth implant of claim 10 wherein the heavy metal is tungsten.

12. The tooth implant of claim 9 wherein the second filler material is a polymer plastic.

13. The tooth implant of claim 12 wherein the tungsten ranges from about 49.5% to about 51% by weight of the mixture.

14. The tooth implant of claim 9 wherein the heavy metal is tungstem particles having a diameter ranging from about 2 to 5 microns.

15. The tooth implant of claim 9 wherein the second filler material is medical grade polysulfone.

* * * * *